(12) United States Patent
Martin

(10) Patent No.: US 6,546,069 B1
(45) Date of Patent: Apr. 8, 2003

(54) COMBINED WAVE DISPERSIVE AND ENERGY DISPERSIVE SPECTROMETER

(75) Inventor: John Martin, The Woodlands, TX (US)

(73) Assignee: Rigaxu/MSC, Inc., The Woodlands, TX (US)

(*) Notice: Subject to any disclaimer, the term of this patent is extended or adjusted under 35 U.S.C. 154(b) by 0 days.

(21) Appl. No.: 10/131,701

(22) Filed: Apr. 24, 2002

(51) Int. Cl.$^7$ ............................................. G01N 23/223
(52) U.S. Cl. ............................................. 378/49; 378/45
(58) Field of Search ............................................. 378/44–50

(56) References Cited

U.S. PATENT DOCUMENTS 5,978,442 A * 11/1999 Kawabara ............... 378/49

* cited by examiner

Primary Examiner—Craig E. Church
(74) Attorney, Agent, or Firm—R. Perry McConnell

(57) ABSTRACT

The invention provides device which is capable of performing both wave dispersive and energy dispersive x-ray fluorescence spectrometry on a single sample, and utilizing a single radiation detector, such as a PIN diode detector.

10 Claims, 2 Drawing Sheets

COMBINED WAVE DISPERSIVE AND ENERGY DISPERSIVE SPECTROMETER

TECHNICAL FIELD

The invention concerns providing wave dispersive and energy dispersive x-ray fluorescence spectrometry capability in a single device.

BACKGROUND OF THE INVENTION

X-ray fluorescent spectroscopy ("XRF") is typically conducted using a wave dispersive spectroscopy ("WDS") or an energy dispersive spectroscopy ("EDS") method. WDS utilizes Bragg diffraction and a precisely placed x-ray detector to determine the intensity of x-rays fluoresced from a sample as a function of wavelength. Because chemical elements have characteristic fluorescent spectra, the information derived from WDS can be used to perform quantitative analysis of the sample's elemental content.

Conversely, EDS samples fluorescent x-rays from a sample without intervening diffraction, and measures x-ray flux as a function of energy. EDS x-ray detectors are typically less expensive than WDS detectors, but also provide lower resolution than WDS detectors. Further, EDS systems are typically less expensive to manufacture, providing a lower-cost alternative to WDS systems.

Because WDS and EDS systems have relative strengths and weaknesses, it is often desirable to have both systems available to perform a full range of XRF analysis on a sample. To somewhat reduce the expense and space requirements of doing so, hybrid WDS/EDS systems have previously been proposed.

For example, U.S. Pat. No. 5,978,442 to Kuwabara discloses an XRF system combining the elements of both WDS and EDS. That system includes a dispersing element used to disperse fluorescent x-rays toward a first x-ray detector, which is utilized in a WDS mode. By retracting the dispersing element from the fluorescent x-ray flux, the flux can be allowed to pass through to a second x-ray detector, which is suitable for and used to conduct EDS measurements.

Similarly, U.S. Pat. No. 4,959,848 to Parobek discloses a hybrid system for determining the thickness of a thin film and quantitative measurement of at least some of its elemental content. This system also involves the use of multiple detectors which are dedicated to either WDS or EDS measurements.

U.S. Pat. No. 6,285,734 to von Alfthan discloses a hybrid WDS/EDS system which requires multiple detectors, including individual monochromators, detectors, and measuring electronics for each element sought to be measured through WDS. Although this system can reduce the time for making measurements by eliminating the need to rotate the WDS x-ray detector through a range of angles, it also multiplies the equipment cost necessary to achieve the desired measurements.

Each of these systems attempts to provide both WDS and EDS measurements through a single apparatus. Such systems may reduce total requirements for laboratory space and utilities needed for operation, but they retain the expense of multiple detection systems, and each apparatus must be large enough to accommodate at least two sets of detectors with their appropriate hardware.

Thus, it is desirable to provide an apparatus capable of performing both WDS and EDS utilizing a single x-ray detector, thus reducing space requirements and overall cost of the apparatus. Further, such an apparatus can be efficiently switched from WDS mode to EDS mode or vice versa, providing great flexibility in utilizing the device to perform needed measurements.

BRIEF DISCLOSURE OF THE INVENTION

As is typical in XRF spectroscopy, the sample from which measurements are taken is irradiated by an x-ray source, producing a flux of fluorescent x-rays from the sample's surface. In WDS mode, the fluorescent x-ray flux is directed through a collimator and then to the surface of a rotatable crystal. For this invention, the rotatable crystal is preferably a multi-layer crystal such as OV-055A produced by Osmic, Inc. The fluorescent x-ray flux undergoes Bragg diffraction in the surface region of the rotatable crystal.

The invention also comprises an x-ray detector, mounted on a goniometer. In the preferred embodiment, the x-ray detector is a PIN diode detector such as PF1000 produced by Moxtek. Such a detector may be switched from a pulse mode to a cascade mode, allowing the detector to be used to perform WDS in pulse mode and EDS in cascade mode. This mode-switching capability increases the counter's efficiency in each mode.

The goniometer provides controlled rotation of the x-ray detector about an arc. In WDS mode, the goniometer and the rotatable crystal are linked so that rotation of the rotatable crystal through an angle θ will move the detector through an angle 2θ, thus maintaining the required positional relationship for measurements resulting from Bragg diffraction.

The goniometer is also aligned so that positioning at one of its endpoints of rotation positions the x-ray detector collinear with the fluorescent x-ray flux from the sample. In this position, the surface of the rotatable crystal is parallel to the fluorescent x-ray flux, so that the rotatable crystal no longer interacts with the x-ray flux. In this position, the detector is preferably switched to cascade mode for the purpose of performing EDS. To provide sufficient x-ray flux during EDS operations, it is preferred that the collimator is retracted from the x-ray flux, either by linkage to the goniometer or by another mechanism which provides for movement of the collimator.

To perform WDS, the x-ray detector is switched to pulse mode and rotated by the goniometer out of the EDS position. The linkage between the goniometer and the rotatable crystal will simultaneously bring the rotatable crystal into position so that Bragg diffraction occurs. In WDS mode, the collimator is inserted into the fluorescent x-ray flux.

It is also preferred that the total 2θ range of the goniometer is restricted to approximately 50°. Although goniometers with greater range are available and although this limit may preclude exhaustive WDS analysis, this range of motion will provide adequate implementation of WDS for most purposes and allows the overall size of the apparatus to remain within desired limits.

DESCRIPTION OF THE PREFERRED EMBODIMENT

Figure 1A:
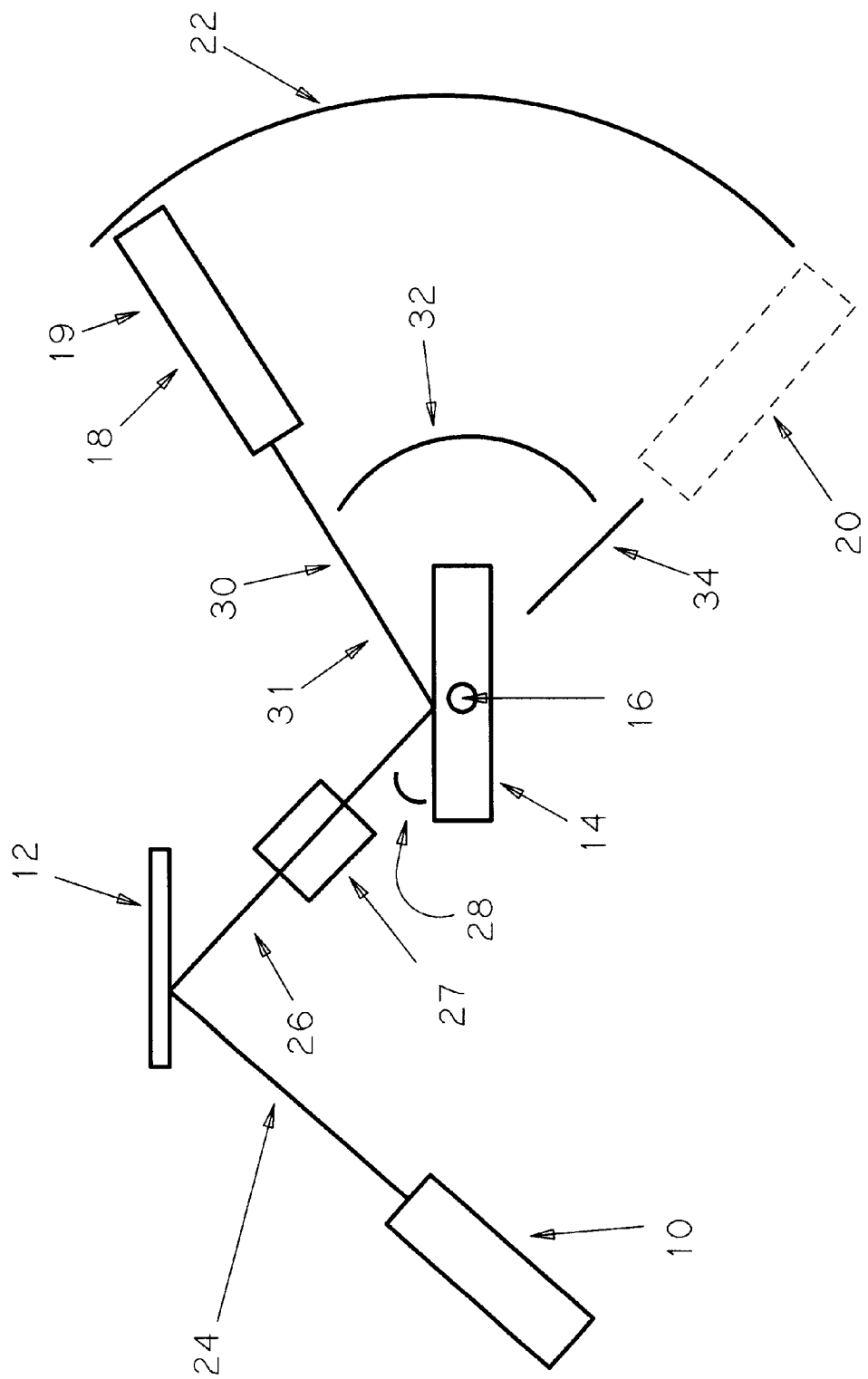
FIG. 1A is a schematic view of an embodiment of the invention positioned for WDS measurements.
Figure 1B:
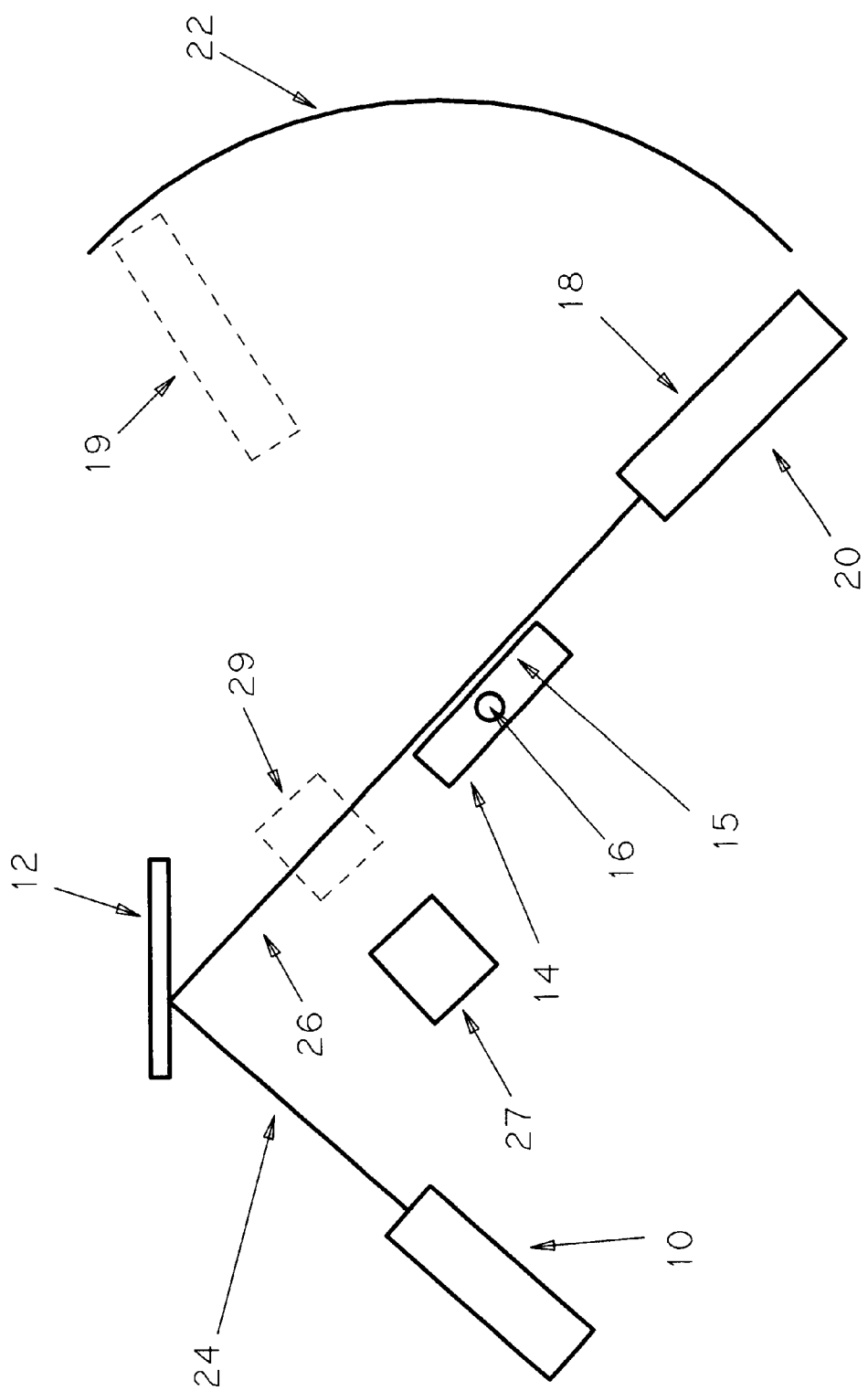
FIG. 1B is a schematic view of the same embodiment of the invention positioned for EDS measurements.

Referring to FIGS. 1A and 1B, schematic views of an embodiment of the invention positioned for WDS and EDS measurements, respectively, are shown. An x-ray source 10 irradiates a sample 12 with a flux of x-rays 24, producing a fluorescent x-ray flux 26 from the sample 12. In WDS mode, as depicted in FIG. 1A, the fluorescent x-ray flux 26 is directed through a collimator 27 and then to a rotatable crystal 14, which is preferably a multi-layer crystal. The fluorescent x-ray flux 26 is incident to the rotatable crystal 14 at an incidence angle 28, generally denoted as θ. The fluorescent x-ray flux undergoes Bragg diffraction by interaction with the rotatable crystal 14, resulting in a diffracted x-ray flux 30 which is detected by an x-ray detector 18. In the preferred embodiment, the x-ray detector 18 is a PIN diode detector and is operated in pulse mode while performing WDS measurements.

The x-ray detector 18 is moved along an arc 22 by a goniometer (not shown). The motion of the x-ray detector 18 is coupled to the rotation of the rotatable crystal 14 about axis of rotation 16 so that x-ray detector 18 moves through a change along angle 32 of 2Δθ for every Δθ change in incidence angle 28. Angle 32 is the angle between the original path-line 34 of the fluorescent x-ray flux 26 and the path-line 31 of the Bragg-diffracted x-ray flux 30. The x-ray detector 18 is movable between first and second endpoints 19 and 20 for purposes of making WDS measurements. At second endpoint 20, the x-ray detector 18 is collinear with the original path-line 34 of the fluorescent x-ray flux 26, and will thus be in position for performing EDS measurements. In the preferred embodiment, the range of movement of the x-ray detector 18 along arc 22 is limited to about 50°, which is sufficient to provide adequate WDS measurements, yet allows the apparatus size and cost to be held within reasonable limits.

As depicted in FIG. 1B, for EDS measurements the x-ray detector 18 is positioned at second endpoint 20 along the arc 22. In this position, the rotatable crystal 14 is positioned so that its surface 15 is parallel to the fluorescent x-ray flux 26, so that Bragg diffraction no longer occurs. It is also possible to translate the rotatable crystal 14 in a linear direction (preferably essentially perpendicular to the fluorescent x-ray flux 26) to further remove it from the fluorescent x-ray flux 26, if necessary. While making EDS measurements, in the preferred embodiment collimator 27 is also removed from its WDS position 29, to maximize the count rate at the x-ray detector 18. While making EDS measurements, the x-ray detector 18 is preferably operated in cascade mode.

I claim:

1. A device for use in performing x-ray fluorescence spectrometry, comprising
   a selectively positionable rotatable crystal,
   an x-ray detector, selectively positionable to detect x-radiation when said rotatable crystal is positioned to permit energy dispersive spectrometry, and further selectively positionable to detect x-radiation when said rotatable crystal is positioned to permit wave dispersive spectrometry.

2. The device of claim 1, wherein said rotatable crystal is a multi-layer crystal.

3. The device of claim 1, wherein said rotatable crystal is selectively positionable around a rotational axis.

4. The device of claim 1, wherein said rotatable crystal is selectively positionable along a linear axis.

5. The device of claim 1, wherein said x-ray detector is positionable by a goniometer.

6. The device of claim 1, wherein said x-ray detector is a PIN diode detector.

7. The device of claim 1, additionally comprising a collimator, wherein said collimator is selectively positionable to condition a flux of fluorescent x-rays prior to detection of such x-rays by said x-ray detector.

8. The device of claim 7, wherein said collimator is positioned out of the flux of fluorescent x-rays when said rotatable crystal is positioned to permit energy dispersive spectrometry.

9. A method of performing x-ray fluorescence spectrometry, comprising,
   irradiating a sample with an x-ray flux to create a flux of fluorescent x-rays from the sample,
   placing a rotatable crystal in the path of the flux of fluorescent x-rays,
   using an x-ray detector to determine the flux of x-rays exigent from said rotatable crystal as a function of the wavelength of the fluorescent x-rays,
   positioning said rotatable crystal so that it does not interact with the flux of fluorescent x-rays, and
   using said x-ray detector to determine the flux of the fluorescent x-rays as a function of the energy of the fluorescent x-rays.

10. A method of performing x-ray fluorescence spectrometry, comprising,
    irradiating a sample with an x-ray flux to create a flux of fluorescent x-rays from the sample,
    using an x-ray detector to determine the flux of the fluorescent x-rays as a function of the energy of the fluorescent x-rays,
    placing a rotatable crystal in the path of the flux of fluorescent x-rays, and
    using said x-ray detector to determine the flux of x-rays exigent from said rotatable crystal as a function of the wavelength of the fluorescent x-rays.

* * * * *